(12) United States Patent
Olde et al.

(10) Patent No.: US 11,123,010 B2
(45) Date of Patent: Sep. 21, 2021

(54) APPARATUS AND METHOD FOR PREDICTION OF RAPID SYMPTOMATIC BLOOD PRESSURE DECREASE

(75) Inventors: Bo Olde, Lund (SE); Kristian Solem, Kavlinge (SE)

(73) Assignee: Gambro Lundia AB, Lund (SE)

(*) Notice: Subject to any disclaimer, the term of this patent is extended or adjusted under 35 U.S.C. 154(b) by 1285 days.

(21) Appl. No.: 13/519,067

(22) PCT Filed: Dec. 22, 2010

(86) PCT No.: PCT/EP2010/070546
§ 371 (c)(1),
(2), (4) Date: Aug. 23, 2012

(87) PCT Pub. No.: WO2011/080185
PCT Pub. Date: Jul. 7, 2011

(65) Prior Publication Data
US 2013/0096402 A1    Apr. 18, 2013
US 2013/0274570 A9    Oct. 17, 2013

Related U.S. Application Data

(60) Provisional application No. 61/290,311, filed on Dec. 28, 2009.

(30) Foreign Application Priority Data

Dec. 28, 2009 (SE) .................. 0951028-0

(51) Int. Cl.
*A61B 5/00* (2006.01)
*A61B 5/021* (2006.01)
(Continued)

(52) U.S. Cl.
CPC .......... *A61B 5/4836* (2013.01); *A61B 5/021* (2013.01); *A61B 5/0205* (2013.01);
(Continued)

(58) Field of Classification Search
CPC combination set(s) only.
See application file for complete search history.

(56) References Cited

U.S. PATENT DOCUMENTS 6,334,065 B1 * 12/2001 Al-Ali ................ A61B 5/6814
600/323
8,287,725 B2    10/2012 Sörnmo
(Continued)

FOREIGN PATENT DOCUMENTS

WO    WO 2007/141246    12/2007
WO    WO 2009/116872    9/2009

OTHER PUBLICATIONS

Bassale, Jules. "Hypotension prediction arterial blood pressure variability." Technical report (2001).*
(Continued)

*Primary Examiner* — Christian Jang
*Assistant Examiner* — Mitchell E Alter
(74) *Attorney, Agent, or Firm* — Mueting Raasch Group

(57) ABSTRACT

A monitoring arrangement 100 is configured to predict a rapid symptomatic drop in a subject's blood pressure, e.g. during a medical treatment or when operating aircraft. To this aim, a pulse shape parameter ($p_{ps}$) with respect to a peripheral body part (105) of the subject (P) is repeatedly registered by means of a pulse oximetry instrument (110) adapted to detect light response variations in blood vessels. A respective pulse magnitude measure is calculated based on each of a number of received pulse shape parameters ($p_{ps}$), and a statistical dispersion measure is calculated based on the thus-calculated pulse magnitude measure. It is investigated whether or not the statistical dispersion measure fulfils a decision criterion relative to a reference measure. An output signal (α) is generated if the decision criterion is found to be fulfilled.

30 Claims, 7 Drawing Sheets

(51) Int. Cl.
*A61B 5/024* (2006.01)
*A61M 1/36* (2006.01)
*A61B 5/0205* (2006.01)
*A61M 1/30* (2006.01)
*A61B 5/053* (2021.01)

(52) U.S. Cl.
CPC ...... *A61B 5/02108* (2013.01); *A61B 5/02416* (2013.01); *A61M 1/30* (2013.01); *A61M 1/36* (2013.01); *A61B 5/053* (2013.01); *A61M 2230/30* (2013.01)

(56) References Cited

U.S. PATENT DOCUMENTS

| | | | |
|---|---|---|---|
| 2003/0036689 A1* | 2/2003 | Diab et al. | 600/323 |
| 2004/0254473 A1 | 12/2004 | Miyahara et al. | |
| 2005/0015009 A1* | 1/2005 | Mourad | A61B 5/031 600/438 |
| 2006/0058691 A1 | 3/2006 | Kiani | |
| 2007/0027678 A1 | 2/2007 | Hotho et al. | |
| 2008/0081961 A1* | 4/2008 | Westbrook | A61B 5/0205 600/301 |
| 2008/0188733 A1* | 8/2008 | Al-Ali | A61B 5/0205 600/364 |
| 2009/0018453 A1* | 1/2009 | Banet | A61B 5/02125 600/493 |
| 2009/0272678 A1* | 11/2009 | Sornmo et al. | 210/90 |
| 2011/0144523 A1* | 6/2011 | Storm | A61B 5/0531 600/547 |

OTHER PUBLICATIONS

Mancini et al., Short Term Variability of Oxygen Saturation During Hemodialysis is a Warning Parameter for Hypotesion Appearance, *Computers in Cardiology*, 2008, 35:881-883.

Javed et al., Changes in the Spectral Powers of Finger Photoplethysmographic Waveform Variability in Hemodialysis Patients, *IEEE*, 2009, 3999-4002.

Guyton & Hall, "Circulatory Shock and Physiology of Its Treatment" in Textbook of *Medical Physiology*, Eleventh Edition, Chapter 24. Cover page, publisher's page, and pp. 278-279 enclosed.

PCT International Search Report and Written Opinion for PCT/EP2010/070546 dated Apr. 26, 2011 (14 pages).

International Preliminary Report on Patentability for PCT/EP2010/070546 dated Jul. 4, 2012 (10 pages).

* cited by examiner

APPARATUS AND METHOD FOR PREDICTION OF RAPID SYMPTOMATIC BLOOD PRESSURE DECREASE

This application is a U.S. National Stage Application of International Application No. PCT/EP2010/070546, filed Dec. 22, 2010, which was published in English on Jul. 7, 2011 as International Patent Publication WO 2011/080185 A1, which claims the benefit under 35 U.S.C. 119(e) of U.S. Provisional Application No. 61/290,311, filed Dec. 28, 2009. International Application No. PCT/EP2010/070546 also claims priority to Swedish Application No. 0951028-0, filed Dec. 28, 2009.

TECHNICAL FIELD

The present invention relates generally to detection of the onset of rapid (i.e. acute) symptomatic drop in a subject's blood pressure. More particularly the invention relates to a monitoring apparatus, a medical system, a method, a computer program, and a computer readable medium.

BACKGROUND ART

There exist many situations wherein it is important to detect potential hypotension, and if possible avoid the actual occurrence thereof, for example when performing artificial blood purification. The human body consists of approximately 60% water—a level which is important to maintain for survival. While it is unproblematic to provide the body with new water, disposal of surplus water is a major problem in renal patients. The task of the normal kidney is to remove superfluous fluid from the blood, such as water, urea and other waste products. The resulting urine is transferred to the bladder and finally leaves the body during urination. The kidney's second task is to regulate for example the balance of acid and base. With malfunctioning kidneys, disorders may develop in most major body organs, a syndrome called uraemia. If uraemia remains untreated, it will lead to death. Uraemia is treated either by kidney transplantation, or some kind of blood treatment, extracorporeal or intracorporeal.

During an artificial blood purification process, such as extracorporeal blood treatment, it is common that the patient suffers from symptomatic hypotension, characterized by a blood pressure drop with symptoms in the form of cramps, nausea, vomiting and sometimes fainting. Such an event is not only strenuous for the patient, but also requires considerable attention from the staff overseeing the treatment. Consequently, during such blood treatment, it is highly desirable to detect the onset of symptomatic hypotension and preventing it from coming about.

However, there are other examples of situations in which it is vital to predict, and if possible prevent, rapid symptomatic hypotension. For instance fighter plane pilots are often subjected to forces that risk result in that the pilot faints. However, also operators of other types of vehicles, crafts and machines may need similar surveillance in order to reduce hazards to the operators, other people and various material goods.

The published US patent application 2004/0254473 describes a laser blood-flow meter and a system for monitoring bio-data of a person. The laser blood-flow meter measures a respective blood flow in different quarters of a biological structure by irradiating laser beams to the structure and detecting resulting scattered beams. Based on the detected light, it is then judged whether the person to which the biological structure belongs is in a serious condition. For example, this judgement may be based on a reduction in blood flow relative to previously recorded standards, reduction in an amplitude of a blood-flow waveform relative to the standards, and a heartbeat frequency increase.

Events of hypotension may be divided into a) "basic hypotension" caused by low blood pressure, b) "acute hypotension" caused by rapidly occurring low blood pressure which may intensify, c) "symptomatic hypotension" caused by low blood pressure and which cause symptoms, d) "rapid symptomatic hypotension" caused by rapid blood pressure decrease with symptoms, and e) "non-acute/acute intradialytic hypotension" caused by slow or rapid blood pressure decrease during dialysis.

Decreased cardiac output will reduce the amount of blood which reaches the capillaries, and thus cause the magnitude of the capillary pulse to decrease. Capillary vasoconstriction is an important autonomic counter regulation in order to prevent hypotension, in which the blood pressure is increased. The blood volume in the capillaries will decrease during capillary vasoconstriction, causing the magnitude of the capillary pulse to decrease. Hence, both increase in cardiac output and elevated capillary vasoconstriction may contribute to preventing intradialytic hypotension, since both factors reflect compensatory mechanisms. Normally these compensatory mechanisms manage to maintain blood pressure. However, failing mechanisms may cause hypotension. Thus, both cardiac output and capillary vasoconstriction will contribute to a decrease in the magnitude of capillary pulse prior to a hypotension.

However, there is yet no solution, which on one hand, provides a quick and reliable hypotension warning, and on the other hand, is cost-efficient and straightforward to implement.

SUMMARY

The object of the present invention is therefore to alleviate the problem above and thus accomplish an uncomplicated solution by means of which the onset of acute symptomatic blood pressure decrease may be detected at a point in time when any effects thereof, still may be avoided.

According to one aspect of the invention, the object is achieved by a monitoring arrangement for predicting rapid symptomatic blood pressure decrease in a subject, the arrangement comprising: a pulse recording means adapted to repeatedly register a pulse shape parameter in a peripheral body part of the subject, wherein the pulse recording means comprises a pulse oximetry instrument adapted to register the pulse shape parameter based on light response variations in at least one blood vessel of the subject, and a control unit adapted to receive the pulse shape parameter, the control unit comprising a processing unit adapted to: calculate, during a measurement period, a respective pulse magnitude measure based on each of a number of received pulse shape parameters, calculate a statistical dispersion measure from the pulse magnitude measures, investigate whether the statistical dispersion measure fulfils a decision criterion relative to a reference measure, and if so, generate an output signal indicating a prediction of said rapid symptomatic blood pressure decrease in the subject.

An important advantage by this design is that an early hypotension warning may be provided based on comparatively small processing resources and sensors being simple and cost-efficient. Moreover, the sensors used are recognized within medicine, and have a well-established functionality.

According to one embodiment, the processing unit is further adapted to: calculate an initial statistical dispersion measure as a function of a set of initial pulse magnitude measures based on the pulse shape parameters received at a first instance, store the initial statistical dispersion measure in a memory means associated with the control unit, calculate, during the measurement period subsequent to the first instance, a respective statistical dispersion measure as a function of a respective set of the pulse magnitude measures, and investigate, for each statistical dispersion measure in the measurement period, whether or not the measure fulfils the decision criterion, which is given relative to the initial statistical dispersion measure.

According to various embodiments, the statistical dispersion measure is any of variance, standard deviation, coefficient of variation, variance-to-mean, a sum of differences, an energy measure, or any combinations or equivalents thereof.

According to various embodiments, the pulse magnitude measure is any of a peak-to-peak measure, an integration measure, an energy measure, and a frequency spectrum intensity measure, or any equivalents thereof.

According to one embodiment, the pulse magnitude measure is based on an average of a number of pulse magnitude measures. Averaging a number of pulse measures may increase the accuracy. For instance, the signal processor may be configured to generate an average temporal shape by: aligning and combining, e.g. based on timing data, a subset of pulse signal segments.

According to one embodiment, the output signal is an alarm triggering signal.

According to one embodiment, the arrangement is connected to a dialysis monitor or machine and configured to activate systems in the dialysis machine to counter-act the occurrence of a hypotension event including any of adjusting a rate of fluid removal from the subject by reducing and/or stopping a rate of fluid removal in case of fulfilled decision criterion, increasing the conductivity in a dialysis fluid, supplying a saline bolus to a blood line connected to the cardiovascular system of the subject, adjusting the positioning of the subject, setting a dialysis monitor in bypass, or any combinations thereof. Hence, the dialysis monitor may execute preventive actions or counter-measurements to prevent and/or reduce the risk of hypotension of the subject.

According to one embodiment, the processing unit is adapted to regard the decision criterion as fulfilled if: an examined statistical dispersion measure of a given set of pulse magnitude measures and/or a sequence of examined statistical dispersion measures is above a threshold value calculated based on the initial statistical dispersion measure, and a predetermined amount of the statistical dispersion measures of the pulse shape parameters received within a test period after the given set of pulse magnitude measures and/or sequence of examined statistical dispersion measures is above the threshold value. The predetermined amount may be a value representing approximately 50% to approximately 100% of the statistical dispersion measures of the pulse shape parameters received within the test period. Alternatively, the predetermined amount represents all the statistical dispersion measures of the pulse shape parameters received within the test period.

According to one embodiment, the test period is an interval selected from a range extending from approximately one minute to approximately fifteen minutes. According to one embodiment, the test period is approximately five minutes long. Thus, depending on the threshold value, based on the predetermined amount of statistical dispersion measures required to fulfil the decision criterion and the test period length selected, a robust and reliable hypotension warning may be obtained for a large variety of subjects and applications.

According to one embodiment, the processing unit is adapted to calculate the threshold value by: normalizing the initial statistical dispersion measure, and dividing the normalized statistical dispersion measure by a predefined denominator. Hence, an unbiased comparison with the initial status may be made.

According to one embodiment, the processing unit is adapted to, during the measurement period, calculate a statistical dispersion measure for a received pulse shape parameter by dividing an original measure with the initial statistical dispersion measure.

According to one embodiment, the predefined denominator is a value selected from a range extending from approximately 0.2 to approximately 0.8. Hence, by selecting the threshold value, the algorithm may be calibrated regarding the length of the test period to attain a desired balance between early warning and false alarms. Generally, however, a relatively small denominator requires a comparatively short test period, and vice versa.

According to an alternative embodiment, the threshold value is given by a predefined dispersion value.

According to one embodiment, the processing unit is further adapted to investigate whether the pulse magnitude measure fulfils a second decision criterion relative to a second reference measure, and generate the output signal as a function of both said decision criterion and said second decision criterion. Thereby, two different techniques for predicting rapid symptomatic blood pressure decrease are combined, which may, e.g., serve to decrease the number of false alarms, improve robustness to signal artefacts, enable prediction for a larger population of subjects, and enable separation of the phenomena behind hypotension. The techniques may, but need not, operate on the same pulse shape parameters.

According to one embodiment, the arrangement further comprises an auxiliary recording means adapted to repeatedly register a bio-impedance parameter representing a degree of contraction of the subject's capillary blood vessels, and the processing unit is further adapted to receive the bio-impedance parameter, investigate whether or not the bio-impedance parameter fulfils an auxiliary alarm criterion, and if so, generate the output signal. Hence, a complementary hypotension detection means is provided, and thereby a more reliable function.

According to one embodiment, the arrangement is further adapted to predict rapid symptomatic blood pressure decrease in a subject undergoing blood treatment, and the processing unit is adapted to calculate the initial statistical dispersion measure based on a set of pulse magnitude measures calculated during an initial phase of the blood treatment. Thus, the hypotension detection is based on a reference measure being relatively unaffected by the treatment. This further enhances the reliability.

According to a second aspect of the invention, the object is achieved by a medical system adapted to perform blood treatment of a subject, wherein the system comprises: a dialysis machine adapted to perform extracorporeal blood treatment of the subject and the alarm arrangement according to the first aspect of the invention. In addition to the above-proposed arrangement, the system includes a dialysis machine adapted to perform extracorporeal blood treatment of a subject. Hence, blood treatment and hypotension surveillance may be effected in parallel in a straightforward manner.

According to a third aspect of the invention, the object is achieved by a control unit for predicting rapid symptomatic blood pressure decrease in a subject, the control unit comprising: an input for receiving pulse shape parameters from a pulse recording means adapted to repeatedly register a pulse shape parameter in a peripheral body part of the subject, wherein the pulse recording means comprises a pulse oximetry instrument adapted to register the pulse shape parameter based on light response variations in at least one blood vessel of the subject; and a processing unit adapted to: calculate, during a measurement period, a respective pulse magnitude measure based on each of a number of received pulse shape parameters, calculate a statistical dispersion measure from the pulse magnitude measures, investigate whether the statistical dispersion measure fulfils a decision criterion relative to a reference measure, and generate an output signal indicating a prediction of said rapid symptomatic blood pressure decrease in the subject.

According to a fourth aspect of the invention, the object is achieved by a method of predicting rapid symptomatic blood pressure decrease in a subject, the method comprising: registering a pulse shape parameter in respect of a peripheral body part of the subject at repeated occasions, investigating, for each pulse shape parameter, whether or not the pulse shape parameter fulfils a decision criterion, and if so, causing an output signal to be generated. The registering of the pulse shape parameter involves a pulse oximetry measurement wherein the pulse shape parameter is determined based on light response variations in at least one blood vessel of the subject. The investigating comprises: calculating, during a measurement period, a respective pulse magnitude measure based on each of a number of received pulse shape parameters, calculating a statistical dispersion measure from the pulse magnitude measures, and investigating whether the statistical dispersion measure fulfils a decision criterion relative to a reference measure. The advantages of this method, as well as the embodiments thereof, are apparent from the discussion hereinabove with reference to the proposed apparatus.

According to a fifth aspect of the invention, the object is achieved by a computer program directly loadable into the internal memory of a computer, comprising software for controlling the proposed method.

According to a sixth aspect of the invention, the object is achieved by a computer readable medium, having a program recorded thereon, where the program is to make a computer control the above proposed method.

According to a seventh aspect of the invention, the object is achieved by a monitoring arrangement for predicting rapid symptomatic blood pressure decrease in a subject. The monitoring arrangement comprises: means for registering a pulse shape parameter in respect of a peripheral body part of the subject at repeated occasions, means for investigating, for each pulse shape parameter, whether or not the pulse shape parameter fulfils a decision criterion, and means for causing, if the pulse shape parameter fulfils the decision criterion, an output signal to be generated, wherein the means for registering is adapted to obtain the pulse shape parameter from a pulse oximetry instrument which is adapted to determine the pulse shape parameter based on light response variations in at least one blood vessel of the subject, and wherein the means for investigating comprises: means for calculating, during a measurement period, a respective pulse magnitude measure based on each of a number of received pulse shape parameters; means for calculating a statistical dispersion measure from the pulse magnitude measures; and means for investigating whether the statistical dispersion measure fulfils a decision criterion relative to a reference measure.

According to a eighth aspect of the invention, the object is achieved by a monitoring arrangement for predicting rapid symptomatic blood pressure decrease in a subject, the arrangement comprising: a pulse recording means adapted to repeatedly register a pulse shape parameter in a peripheral body part of the subject, and a control unit adapted to receive the pulse shape parameter, investigate whether or not the pulse shape parameter fulfils a decision criterion, and if so, cause an output to be generated, the pulse recording means comprising a pulse oximetry instrument adapted to register the pulse shape parameter based on light response variations in at least one blood vessel of the subject, and the control unit comprises a processing unit adapted to: calculate, during a measurement period, a respective pulse magnitude measure based on each of a number of received pulse shape parameters, calculate a statistical dispersion measure from the pulse magnitude measures, investigate whether the statistical dispersion measure fulfils a decision criterion relative to a reference measure, and generate an output signal.

Embodiments of the second to eighth aspects of the invention may correspond to the above-identified embodiments of the first aspect of the invention.

The generated output signal may be an alarm signal or trigger for a treatment monitor such as a dialysis monitor to initiate an operating mode to prevent a hypotension event from occurring.

Still other objectives, features, aspects and advantages of the present invention will appear from the following detailed description, from the attached claims as well as from the drawings.

BRIEF DESCRIPTION OF THE DRAWINGS

The present invention is now to be explained more closely by means of preferred embodiments, which are disclosed as examples, and with reference to the attached drawings.

DETAILED DESCRIPTION OF EXEMPLARY EMBODIMENTS

In the context of this specification, capillary pulse refers to volume changes in peripheral vessels. Furthermore, hypotension, a hypotension event and the like are examples of a condition involving rapid symptomatic blood pressure decrease.

Figure 1:
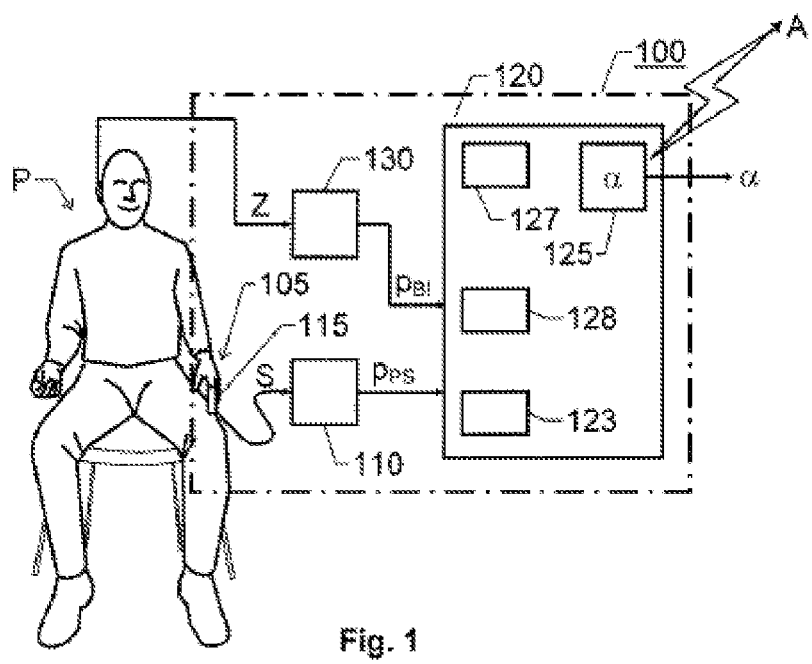
FIG. 1 shows a schematic image of an alarm arrangement according to one embodiment of the invention.

We refer initially to FIG. 1, which depicts a monitoring arrangement 100 for predicting rapid symptomatic blood pressure decrease in a subject P according to one embodiment of the invention. The arrangement 100 includes a pulse recording means 110 and 115, and a control unit 120.

The pulse recording means has a pulse oximetry instrument 110, and preferably a separate sensor unit 115. This unit 115 includes at least one light source and at least one light detector through which a pulse signal S is registered that describes light response variations, including pulses, in at least one blood vessel in a peripheral body part 105 of the subject P (e.g. in a finger, a toe, an earlobe, a nose tip or other extremity, in the skin thereof, or in the skin of any other body part) depending on where the sensor unit 115 is attached to the subject P. The light response variations preferably reflect variations in the absorption of the light transmitted from said at least one light source. However, light reflectance and/or light transmittance may equally well be studied. In any case, the pulse oximetry instrument 110 is adapted to register a pulse shape parameter $p_{PS}$ based on the pulse signal S.

As used herein, a "pulse shape parameter $p_{PS}$" refers to a signal segment in, or derived from, the pulse signal S, i.e. a sequence of signal values within a time window. A sequence of pulse shape parameters $p_{PS}$ thus represent different signal segments in the pulse signal S, where the signal segments may or may not be overlapping. The signal segment may, but need not, be selected so as to contain at least part of at least one pulse in the pulse signal S. From each pulse shape parameter $p_{PS}$, the control unit 120 is adapted to calculate a pulse magnitude measure PM. As will be described in more detail below, the pulse magnitude measure PM represents the magnitude of the signal values in the signal segment. Within the context of this specification, a pulse power measure is the same as a pulse magnitude measure.

Thus, the control unit 120 is adapted to receive and process the pulse shape parameter $p_{PS}$. Specifically, the control unit 120 includes a processing unit 128, which may be adapted to store received data, or data generated during processing, in a memory means 123. The memory means 123 is either included in the control unit 120, or associated thereto, e.g. via a cable or a wireless connection.

Figure 2:
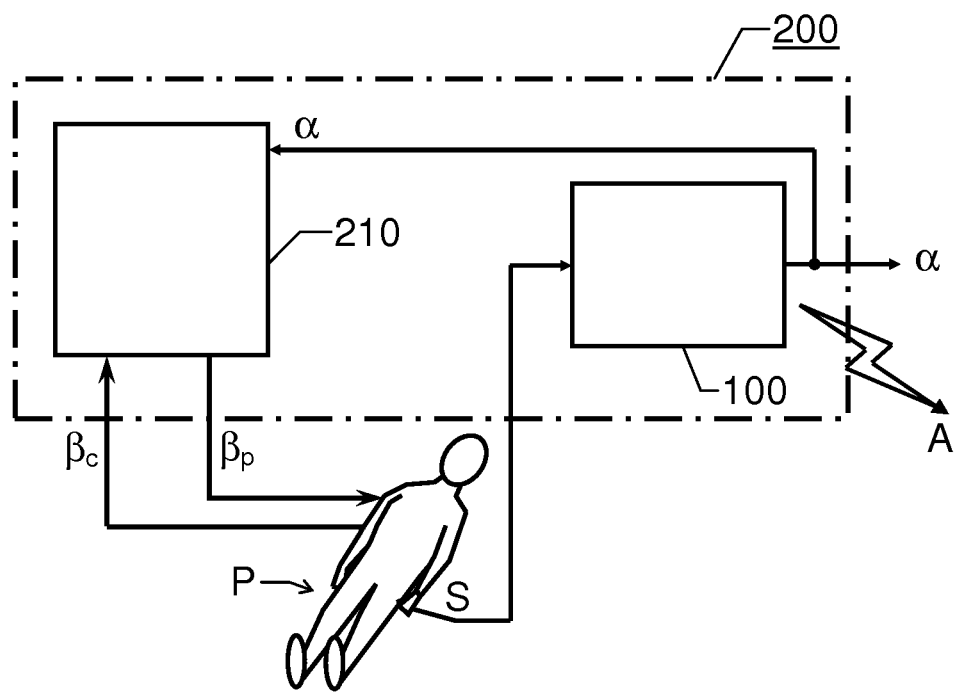
FIG. 2 is a block diagram of a medical system according to one embodiment of the invention.

Turning to FIG. 2, a block diagram is shown for a medical system 200 according to one embodiment of the invention for performing blood treatment of a subject P. To this aim, the system 200 includes a dialysis machine 210, which may be adapted to perform extracorporeal blood treatment of the subject P, i.e. the machine 210 is adapted to extract contaminated blood $\beta_c$ from the subject P and return purified blood $\beta_p$ to the subject P. The system 200 also includes the above-described monitoring arrangement 100 for predicting any rapid blood pressure decreases being potentially unhealthy to the subject P. Thus, in parallel with cleaning the subject's P blood, the monitoring arrangement 100 monitors him/her regarding the risk that acute symptomatic hypotension occurs. In case of an alarm signal α, the overseeing staff may be informed and/or the dialysis machine 210 may be controlled to adjust its treatment parameter in order to avoid a hypotension situation. This type of adjustment is symbolized by means of a feedback signal α from the monitoring arrangement 100 to the dialysis machine 210.

As will be further explained below, the control unit (monitoring device) 120 operates to detect fulfilment of a predetermined decision criterion, which fulfilment may be taken as an indication of an upcoming hypotension event and bring the control unit 120 to activate an alarm A and/or output the alarm signal α, which may be followed by further actions to counter-act the occurrence of a hypotension event and/or reducing negative consequences to the subject where an hypotension event is unavoidable. Such actions may include:

i. Stopping or decreasing the rate of ultrafiltration (UFR),
ii. Optimizing fluid removal by regulating the UFR, temporarily lowering or stopping the UFR in case of reached decision criterion,
iii. Increasing the conductivity in the dialysis fluid to increase refilling of the subject's blood circulation in order to increase the blood pressure and thus reduces the risk of hypotension,
iv. Supply a saline bolus to the blood line, i.e. a small yet concentrated amount of saline to increase refilling of the subject's blood circulation in order to increase the blood pressure and thus reduces the risk of hypotension,
v. Adjust the positioning of the subject to increase the blood volume to the head, e.g. by changing the subject's head and feet according to the so called "Trendelenburg position", for instance by controlling the structure of a bed or chair,
vi. Setting the dialysis monitor in bypass, i.e. temporarily stopping the dialysis process.

Noticeable is the function in ii), allowing maximal fluid to be drawn from the patient during a treatment, while yet avoiding the subject from suffering from hypotension.

Below follows a description of two main embodiments for predicting rapid symptomatic blood pressure decrease in the subject P, denoted "pulse magnitude embodiment" and "dispersion embodiment", as well as a combination of the two.

I. Pulse Magnitude Embodiment

According to the pulse magnitude embodiment, the control unit 120 is adapted to predict rapid symptomatic blood pressure decrease in the subject P based on an initial pulse magnitude measure PM1 calculated from one or more pulse shape parameters $p_{PS}$ received or obtained from the pulse oximetry instrument 110 during an initial phase e.g. of the blood treatment when the subject is still relatively unaffected by the treatment.

Figure 5A:
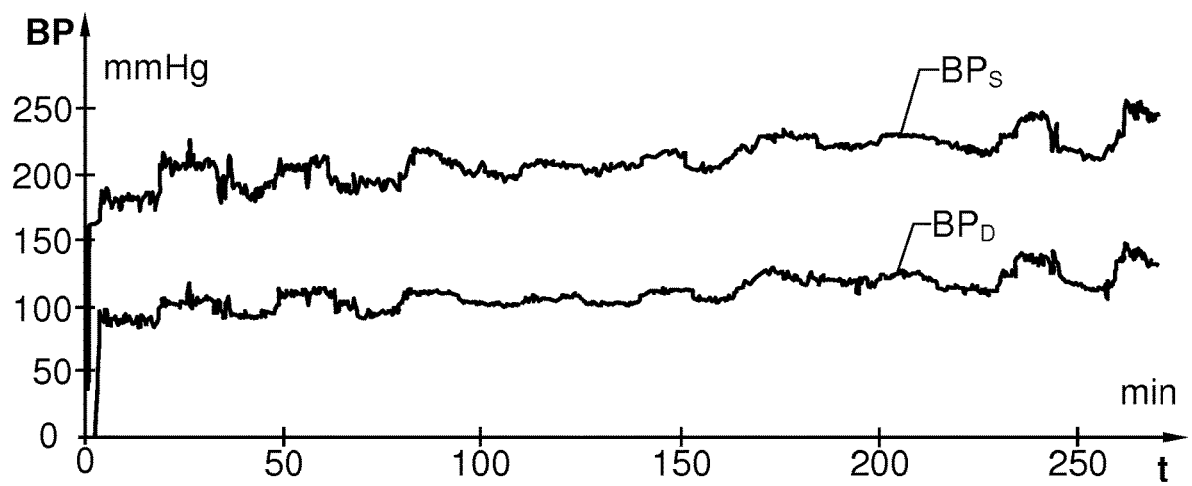
FIG. 5a is a graph illustrating an example of a first subject's blood pressure variation during a blood treatment process.
Figure 5B:
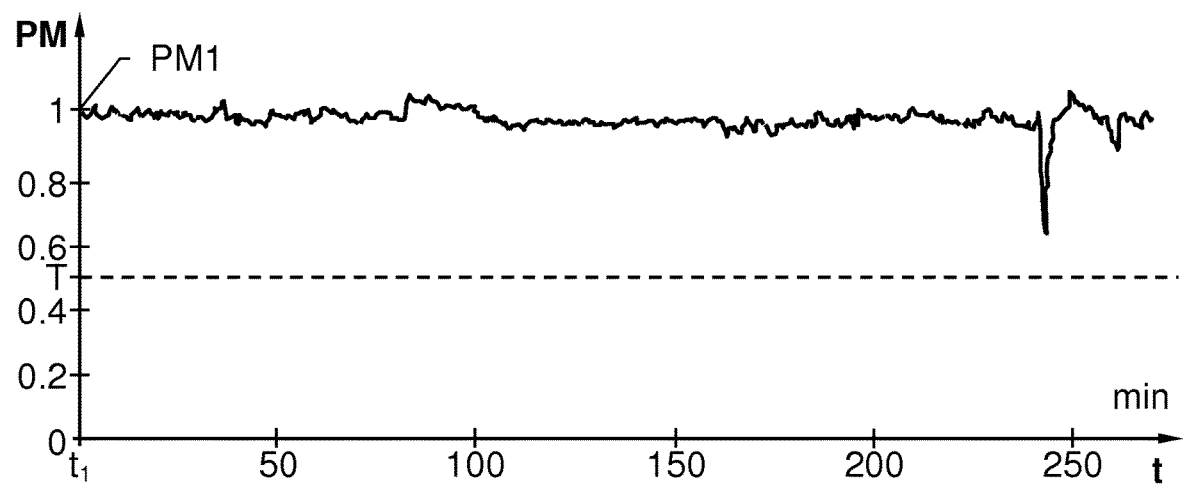
FIG. 5b is a graph illustrating how a pulse magnitude measure of the first subject varies over time.

FIG. 5b shows a graph, which illustrates the initial pulse magnitude measure PM1 in respect of a first subject being exposed to an extracorporeal blood treatment, as well as subsequently calculated pulse magnitude measures PM. Preferably, the initial pulse magnitude measure PM1 is not only derived from a singular pulse shape parameter $p_{PS}$, but is rather based on an average of a number of such parameters registered during an initial measurement period. The graph in FIG. 5b represents time t in minutes along the horizontal axis, and the pulse magnitude measure PM along the vertical axis.

According to embodiments of the invention, the processing unit 128 may determine the pulse magnitude measure PM via any one of number of different strategies.

In one alternative, the pulse magnitude measure PM is given by the difference between a maximum and a minimum value of the pulse shape parameter $p_{PS}$, where the pulse shape parameter $p_{PS}$ is selected to contain at least one pulse. Below, this measure is also denoted "peak-to-peak measure". If the pulse shape parameter $p_{PS}$ contains plural pulses, the pulse magnitude measure PM may alternatively be given by an average of the different peak-to-peak measures for the pulses in the pulse shape parameter $p_{PS}$.

In another alternative, the pulse magnitude measure PM is given by an integration of the signal values in the pulse shape parameter $p_{PS}$, optionally with respect to a base line, e.g. given by a minimum value in the pulse shape parameter $p_{PS}$. The integration may be given by a sum of values, a sum of absolute values, a sum of (absolute) differences between the signal values and an average of the signal values in the pulse shape parameter $p_{PS}$, or any equivalent function.

In another alternative, the pulse magnitude measure PM is given by a power or energy measure such as root mean square (RMS) of the pulse shape parameter $p_{PS}$, or any equivalent function. The use of RMS may require a prior calibration of the pulse shape parameters $p_{PS}$ to a zero average.

In yet another alternative, the pulse magnitude measure PM is obtained by a frequency analysis of the pulse shape parameter $p_{PS}$, e.g. as an intensity of one or more frequency components in an energy spectrum obtained by Fourier analysis of the pulse shape parameter $p_{PS}$.

FIG. 5a is a graph illustrating the first subject's systolic and diastolic blood pressure variations $BP_S$ and $BP_D$ respectively in mmHg during the treatment. It should be understood that the blood pressure data in FIG. 5a has been obtained by a dedicated instrument connected to the subject for the sole purpose of demonstrating that the pulse magnitude measure is useful in predicting a rapid symptomatic blood pressure decrease in the subject. The blood pressure BP varies throughout the treatment. However, as seen in FIG. 5a, no hypotension occurs. Apart from a dip around 245 minutes into the treatment, the pulse magnitude measure PM also remains relatively stable (FIG. 5b).

During a measurement period subsequent to the first instance $t_1$ (i.e. here from t=0 and onwards), the processing unit 128 is adapted to calculate a respective pulse magnitude measure PM based on each of a number of received pulse shape parameters $p_{PS}$. This typically means that a time sequence of pulse magnitude measures PM are generated for a time sequence of pulse shape parameters $p_{PS}$. For each pulse magnitude measure PM in the measurement period, the processing unit 128 is further adapted to investigate whether or not the measure PM fulfils a decision criterion relative to the initial pulse magnitude measure PM1. If such a decision criterion is found to be fulfilled, the processing unit 128 is adapted to generate an alarm triggering signal α. The alarm triggering signal α, in turn, is presumed to cause an alarm A to be activated in an alarm unit 125 of the control unit 120 itself, and/or in an external unit receiving the alarm triggering signal α. The pulse magnitude measure PM and the decision criterion will be discussed in detail below with reference to FIGS. 6, 7 and 8.

Figure 6A:
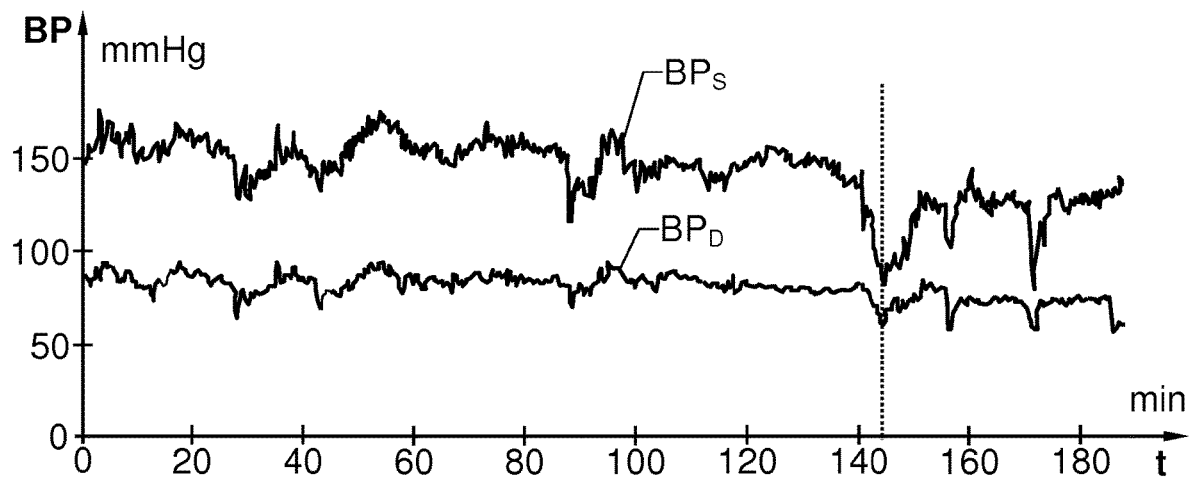
FIG. 6a is a graph illustrating an example of a second subject's blood pressure variation during a blood treatment process.
Figure 7A:
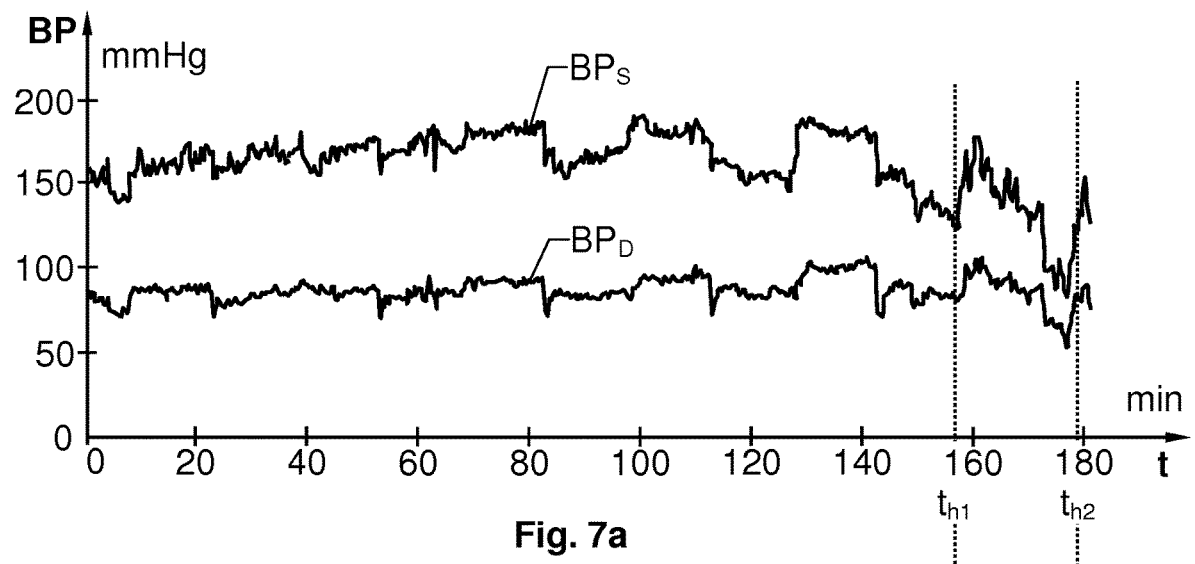
FIG. 7a is a graph illustrating an example of a third subject's blood pressure variation during a blood treatment process.

Turning now to FIG. 6a, we see a diagram with a graph exemplifying how the systolic blood pressure $BP_S$ and the diastolic blood pressure $BP_D$ in mmHg of a second subject varies during an extracorporeal blood treatment. At a point in time $t_h$ around 145 minutes into the treatment, the subject suffers from acute symptomatic hypotension. This event is preceded by a rapid BP decrease in both the systolic $BP_S$ and diastolic $BP_D$ blood pressures.

Figure 6B:
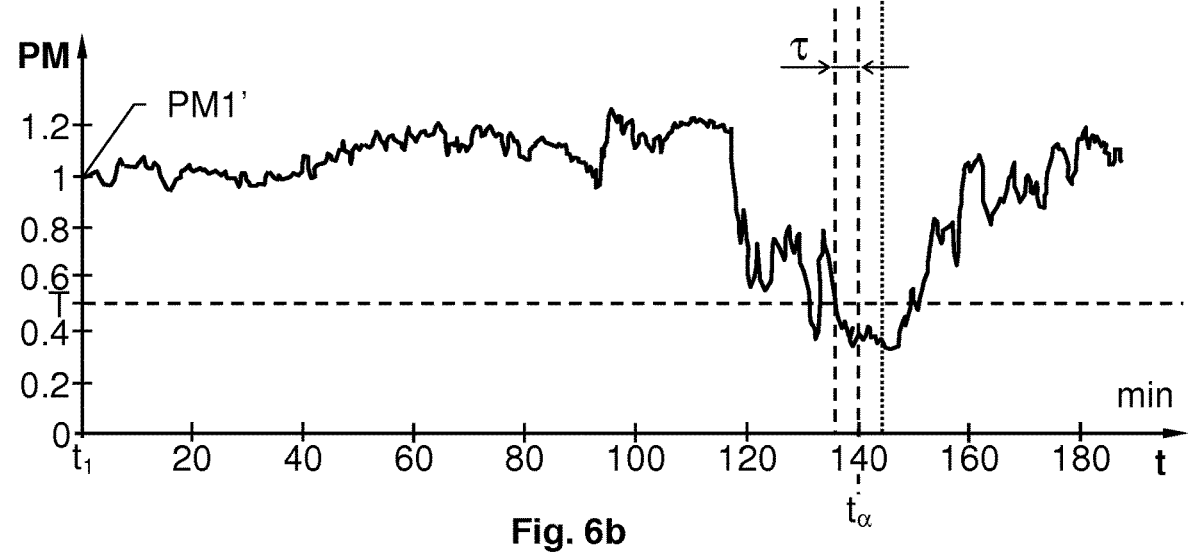
FIG. 6b is a graph illustrating how a pulse magnitude measure of the second subject varies over time.

Referring further to FIG. 6b, we will now explain how the proposed pulse magnitude measure PM and a reference measure or threshold value T are calculated according to embodiments of the invention, and how evaluation of these measures is used to predict the hypotension event.

The processing unit 128 of FIG. 1 is adapted to investigate whether a decision criterion is fulfilled with respect to the pulse shape parameters $p_{PS}$ received during the measurement period. In this example, the measurement period starts at t=0, and the period continues throughout the interval covered by the diagrams of FIGS. 6a and 6b. The processing unit 128 of the control unit 120 may calculate the threshold value T as follows. First, the initial pulse magnitude measure PM1' derived at $t_1$ (i.e. here t=0) is normalized. In this example PM1'=1, however technically, any other reference is conceivable. Then the normalized value is divided by a predefined denominator, which may be any number between 1.2 and 5, e.g 2. As a result, the threshold value T is obtained. Consequently, given that the predefined denominator is 2, T becomes 0.5 as illustrated in FIG. 6b by a dashed line. In the measurement period after $t_1$, the processing unit 128 calculates a normalized pulse magnitude measure PM for each received pulse shape parameter $p_{PS}$ by dividing an original magnitude measure with the normalized initial pulse magnitude measure PM1' (which is derived from the pulse shape parameter $p_{PS}$ received at the first instance $t_1$). Hence, a pulse magnitude measure PM representing a larger pulse magnitude than that of the pulse shape parameter $p_{PS}$ received at the first instance $t_1$ results in a pulse magnitude measure PM>1, and conversely, a pulse magnitude measure PM representing a smaller pulse magnitude than that of the pulse shape parameter $p_{PS}$ received at the first instance $t_1$ results in a pulse magnitude measure PM<1.

When the pulse magnitude measure PM has been derived, the processing unit 128 regards the above-mentioned decision criterion to be fulfilled if:
  i. an examined pulse magnitude measure PM of a given pulse shape parameter is below the threshold value T; and
  ii. a predetermined amount of the pulse magnitude measures PM of the pulse shape parameters $p_{PS}$ received within a test period τ after the given pulse shape parameter are below the threshold value T.

According to one embodiment of the invention, the predetermined amount is a value representing approximately 50% to approximately 100% of the pulse magnitude measures PM of the pulse shape parameters $p_{PS}$ received within the test period τ. The predetermined amount may represent all the pulse magnitude measures PM of the pulse shape parameters $p_{PS}$ received within the test period τ. Nevertheless, to avoid interruption by singular pulse magnitude measures PM above the threshold value T, it may be advantageous to assign a predetermined amount equivalent to less than 100%. Alternatively, a secondary threshold value may be assigned somewhat above the threshold value T, and the processing unit 128 may employ a hysteresis algorithm, such that once the pulse magnitude measures PM has fallen below the threshold value T, the decision criterion is deemed fulfilled if, at expiry of the test period τ, the pulse magnitude measures PM has not exceeded the secondary threshold value.

In the example illustrated in FIG. 6b, the pulse magnitude measure PM for the first time falls below the threshold value T around t=128 minutes. Here, we assume that the above-mentioned predetermined amount is 100%, and that the test period τ is 5 minutes long. Hence, the test period τ ends around t=133 minutes. At this point in time, however, the pulse magnitude measure PM again exceeds the threshold value T. Therefore, no alarm triggering signal will be generated by the processing unit 128.

Around t=135 minutes, the pulse magnitude measure PM returns to a level below the threshold value T, and this time the pulse magnitude measure PM remains below the threshold value T for period exceeding the test period τ (here 5 minutes). Consequently, at the end of the test period τ (i.e. at approximately t=140 minutes), the processing unit generates the alarm triggering signal α. It is then around 5 minutes left until t=$t_h$ when hypotension occurred. Thus, aided by the alarm triggering signal α, it had been possible to perform appropriate, manual and/or automatic, hypotension inhibiting actions in due time. It is further advantageous if the processing unit 128 is adapted to generate an attention signal (e.g. causing a yellow lamp on the unit to be lit up) whenever the pulse magnitude measure PM is below the threshold value T. Thus, any supervising staff may obtain an earliest possible indication of that acute symptomatic hypotension may be forthcoming, and that therefore the subject needs extra attention. If, at the end of the pulse magnitude measure PM rises above the threshold value T without the decision criterion having been fulfilled, the attention signal is deactivated.

Of course, in embodiments of the invention, a test period τ of length other than five minutes is likewise conceivable. In fact, the test period τ may represent any interval selected from a range extending from approximately one minute to approximately fifteen minutes. The length of the test period τ is a design parameter that is selected to attain a desired balance between robustness and reliability. Preferably, the choice of the test period τ is made conjoint with the predefined denominator above. Namely, for a given balance between early hypotension warning and false alarms, a relatively large denominator requires a comparatively short test period, and vice versa.

Moreover, if in the example of FIG. 6b, the predetermined amount of pulse magnitude measure PM below the threshold value T required to fulfil the decision criterion had been selected to a value less than 100%, say 60%, the alarm triggering signal α would have been generated already at expiry of the first test period τ (i.e. around t=133 minutes).

Analogous to FIGS. 6a and 6b, FIGS. 7a and 7b are graphs exemplifying a third subject's blood pressure variation during an extracorporeal blood treatment and a corresponding pulse magnitude measure variation respectively.

In this example, the subject suffers from two acute symptomatic hypotension events at t=$t_{h1}$ (around 155 minutes into the treatment) and at t=$t_{h2}$ (around 178 minutes into the treatment) respectively. To facilitate comparison with the previous examples, we have also here chosen to normalize the initial pulse magnitude measure PM1" derived at $t_1$ (t=0) to 1, selected a threshold value T=0.5 (i.e. the predefined denominator is 2), and set the length of the test period τ to five minutes. Furthermore, we regard the decision criterion as fulfilled if all pulse magnitude measures PM of the pulse shape parameters $p_{PS}$ received within the test period τ fall below the threshold value T.

Figure 7B:
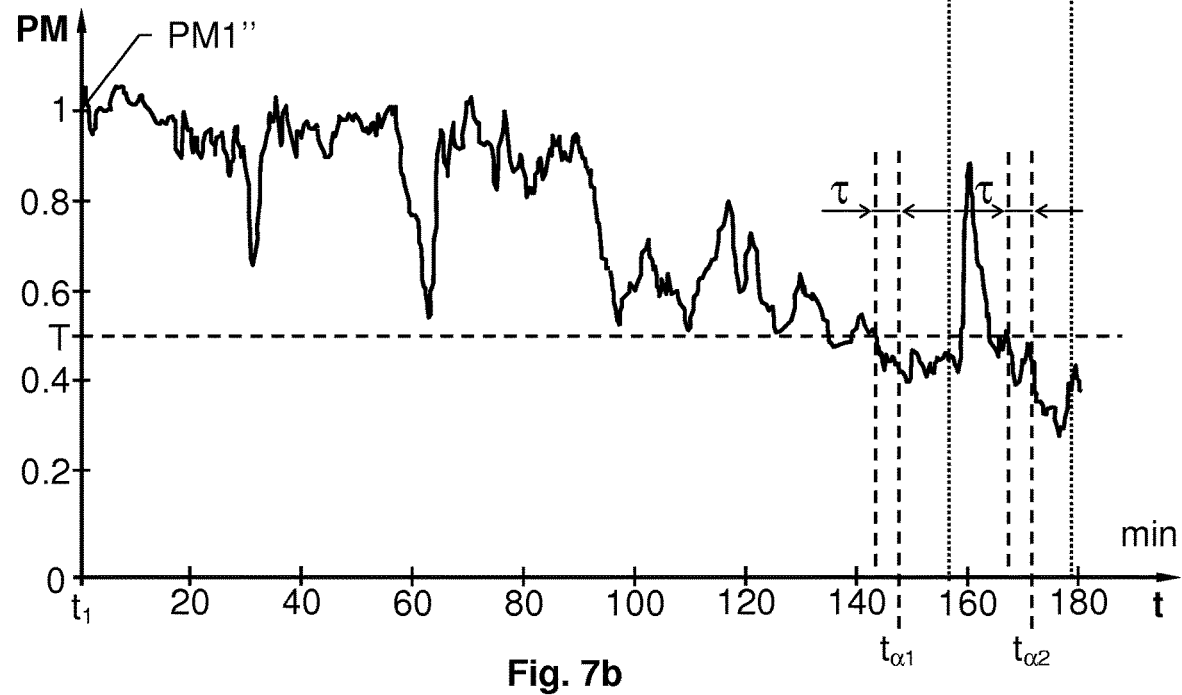
FIG. 7b is a graph illustrating how a pulse magnitude measure of the third subject varies over time.

As is apparent from the diagram in FIG. 7b, given these parameter values, the processing unit 128 will generate the alarm triggering signal α at t=$t_{α1}$ (around 145 minutes into the treatment) and at t=$t_{α2}$ (around 171 minutes into the treatment) respectively. Thus approximately seven to ten minutes advance indications of the upcoming hypotension events are provided.

Returning briefly to FIG. 5b, we see that the pulse magnitude measure PM here never falls below the threshold value T (here 0.5). Thus, in this case, the processing unit 128 will not generate any alarm triggering signal α.

We now return to FIG. 1. According to one embodiment of the invention, the arrangement 100 includes an auxiliary recording unit 130 adapted to repeatedly register a bio-impedance parameter $p_{BI}$ that represents a degree of contraction of the subject's P capillary blood vessels. In this embodiment, the processing unit 128 is further adapted to receive or obtain this bio-impedance parameter $p_{BI}$, and investigate whether or not the parameter $p_{BI}$ fulfils an auxiliary alarm criterion. If this criterion is found to be fulfilled, the processing unit 128 is adapted to generate the alarm triggering signal α. Hence, the performance and reliability of the arrangement 100 is improved. To further improve the usability of the arrangement 100, it is preferable if the auxiliary recording means 130 is adapted to determine a bio-impedance parameter being essentially unrelated to the contraction of the subject's P capillary blood vessels. Thus, the auxiliary recording means 130 may register an absolute body temperature, variations in the body temperature and/or an amount of sweat on the subject P, and the processing unit may be adapted to test the auxiliary alarm criterion against one or more of these parameters.

An embodiment of a method of predicting rapid symptomatic blood pressure decrease in a subject according to the invention will now be described below with reference to the flow chart in FIG. 8.

A first step 810 investigates whether or not a pulse shape parameter in respect of a peripheral body part of the subject has been received. If no such parameter has been received, the procedure loops back and stays in step 810. If, however, a pulse shape parameter is received, a step 820 follows, which calculates an initial pulse magnitude measure based on a pulse shape parameter received at a first instance. It is here presumed that the pulse shape parameter has been registered by means of a pulse oximetry measurement wherein the pulse shape parameter is determined based on light absorption variations in at least one blood vessel of the subject.

A following step 830, stores the initial pulse magnitude measure in a memory (cf. memory means 123 in FIG. 1). Thereafter, a measurement period follows during which a step 840 calculates a respective pulse magnitude measure based on each received pulse shape parameter. Moreover, for each pulse magnitude measure in the measurement period, an evaluation step 850 subsequent to step 840, investigates whether or not the pulse magnitude measure fulfils a decision criterion relative to the initial pulse magnitude measure. If the decision criterion is found not to be fulfilled, and provided that the measurement period still is active, the procedure loops back to step 840.

However, if it is found in the evaluation step 850 that the decision criterion is fulfilled, a step 860 follows, which causes an output such as an alarm triggering signal to be generated. Thereafter, the procedure may either end, or loop back to the step 840 (provided that the measurement period still is active). The measurement period may be inactivated in response to a manual intervention, such as depressing a reset button. Namely, thereby it is straightforward to resume (or actually maintain) the measurement period even in cases where the measurement may have been involuntary interrupted, for instance due to that the sensor unit 115 has fallen off the subject P. In such cases, the sensor unit 115 may simply be reattached, where after the measurement continues.

II. Dispersion Embodiment

It has surprisingly been found that the dispersion in the sequence of pulse magnitude measures (PM) obtained in accordance with the pulse magnitude embodiment may provide information for predicting an upcoming hypotension event.

The dispersion may be represented by any measure that represents a variability or spread of a sequence of values. Non-limiting examples of potentially useful statistical dispersion measures include standard deviation ($\sigma$), variance ($\sigma^2$), coefficient of variation ($\sigma/\mu$) and variance-to-mean ($\sigma^2/\mu$). Other examples include a sum of differences, e.g. given by $$\sum_{i=2}^{n} |x_i - x_{i-1}|, \text{ or } \sum_{i=1}^{n} \sum_{j=1}^{n} |x_i - x_j|,$$

or an energy measure, such as $$\sum_{i=1}^{n} x_i^2,$$

with n being the number of PM values in the sequence. Yet other examples include a measure based on a sum of absolute differences from an average value m, with the average value m being calculated for the PM values in the evaluation segment using any suitable function, such as arithmetic mean, geometric mean, median, etc. It is to be noted that all of the above suggested statistical dispersion measures also include normalized and/or weighted variants thereof.

Figure 8:
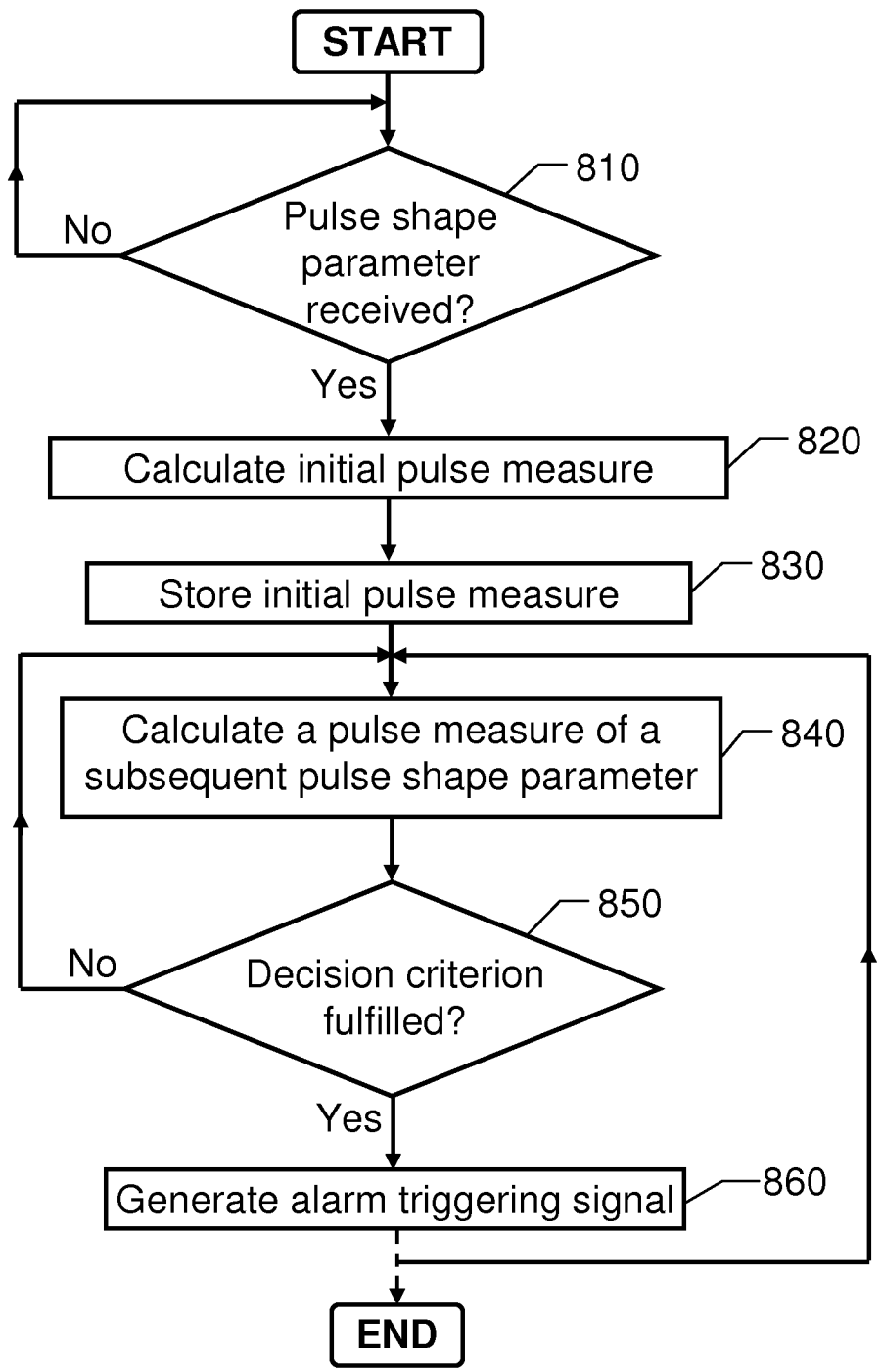
FIG. 8 is a flow diagram which illustrates an embodiment of a method of predicting rapid symptomatic blood pressure decrease.

For an embodiment of a method of predicting rapid symptomatic blood pressure decrease in a subject based on the statistical dispersion measure, reference may be made to the flow chart in FIG. 8. Thus, all steps 810-860 described in relation to FIG. 8 are equally applicable to the statistical dispersion embodiment.

In short, step 810 checks if a pulse shape parameter has been received, and if so, step 820 calculates an initial set of pulse magnitude measures PM1 based on a set of pulse shape parameters $p_{PS}$ received at a first instance, and calculates an initial dispersion measure SM1 based on the set of pulse magnitude measures PM. Here, it should be understood that the initial dispersion measure SM1 represents the variability of the initial set of pulse magnitude measures PM1. Step 830 stores the initial dispersion measure SM1 in memory, wherein the measurement period is started by repeatedly executing steps 840 and 850. Step 840 calculates a respective pulse magnitude measure PM based on each received pulse shape parameter $p_{PS}$. Step 840 also calculates the dispersion measure SM for the thus-calculated pulse magnitude measure PM in combination with pulse magnitude measures PM calculated in previous iterations of steps 840 and 850. For example, the dispersion measure SM may be calculated for a set of the most recently calculated pulse magnitude measures PM. It is conceivable that step 840 is designed to calculate the dispersion measure SM only in certain iterations of steps 840 and 850. For example, every i:th iteration of step 840 may involve a calculation of the dispersion measure SM, whereas every iteration involves a calculation of the pulse magnitude measure PM. Moreover, for each dispersion measure SM in the measurement period, the evaluation step 850 investigates whether or not the dispersion measure SM fulfils a decision criterion relative to the initial dispersion measure SM1.

Furthermore, all embodiments, variants, alternatives, examples and implementations described in relation to the pulse magnitude embodiment are equally applicable to the dispersion embodiment, including the calculation of thresholds, the normalization of the initial measure, and examples of the decision criterion. However, in the dispersion embodiment, the decision criterion is typically fulfilled when the dispersion measure SM exceeds a threshold value T. Thus, in analogy with the examples given for the pulse magnitude embodiment, the threshold value T may be obtained by division with a predefined denominator in the approximate range of 0.2-0.8. In this context, a division by a denominator is equivalent to a multiplication by a predefined factor, e.g. in the range 1.2-5.

It has also been found that the dispersion measure itself may contain information that may be used for predicting an upcoming hypotension event. Thus, depending on implementation, steps 820 and 830 may be omitted, and step 840 may operate without normalization. It is also conceivable, in all embodiments, that the decision criterion (in step 850) uses a predefined threshold or reference measure instead of a threshold determined based on the initial statistical measure (SM1). The predefined threshold may, e.g., be given as an absolute or relative dispersion value.

FIG. 3a is a graph that illustrates pulse magnitude measures PM obtained in respect of a first subject undergoing an extracorporeal blood treatment with no occurrence of hypotension. FIG. 3a illustrates a sequence of pulse magnitude measures PM (peak-to-peak measures) which are calculated for a sequence of non-overlapping pulse shape parameters $p_{PS}$, where the time window of each pulse shape parameter $p_{PS}$ is selected such that it includes approximately one pulse. FIG. 3b illustrates a resulting sequence of variance measures SM, which are calculated based on the peak-to-peak measures in FIG. 3a. FIG. 3a may be seen to include a long-term "DC" level component of the pulse magnitude measure PM, which is used for detection in the pulse magnitude embodiment, and a short-term "AC" component, which may be regarded as a pulse magnitude modulation. This modulation is represented by the variance measure SM in FIG. 3b.

FIG. 4a is graph that illustrates pulse magnitude measures PM obtained in respect of a second subject undergoing an extracorporeal blood treatment and suffering from acute symptomatic hypotension at a point in time ($t_{hyp}$) around 140 minutes into the treatment, as indicated by the dashed line. FIG. 4b illustrates the resulting sequence of variance measures SM. Clearly, the variance measures SM may be evaluated to predict the acute symptomatic hypotension event.

Figure 3:
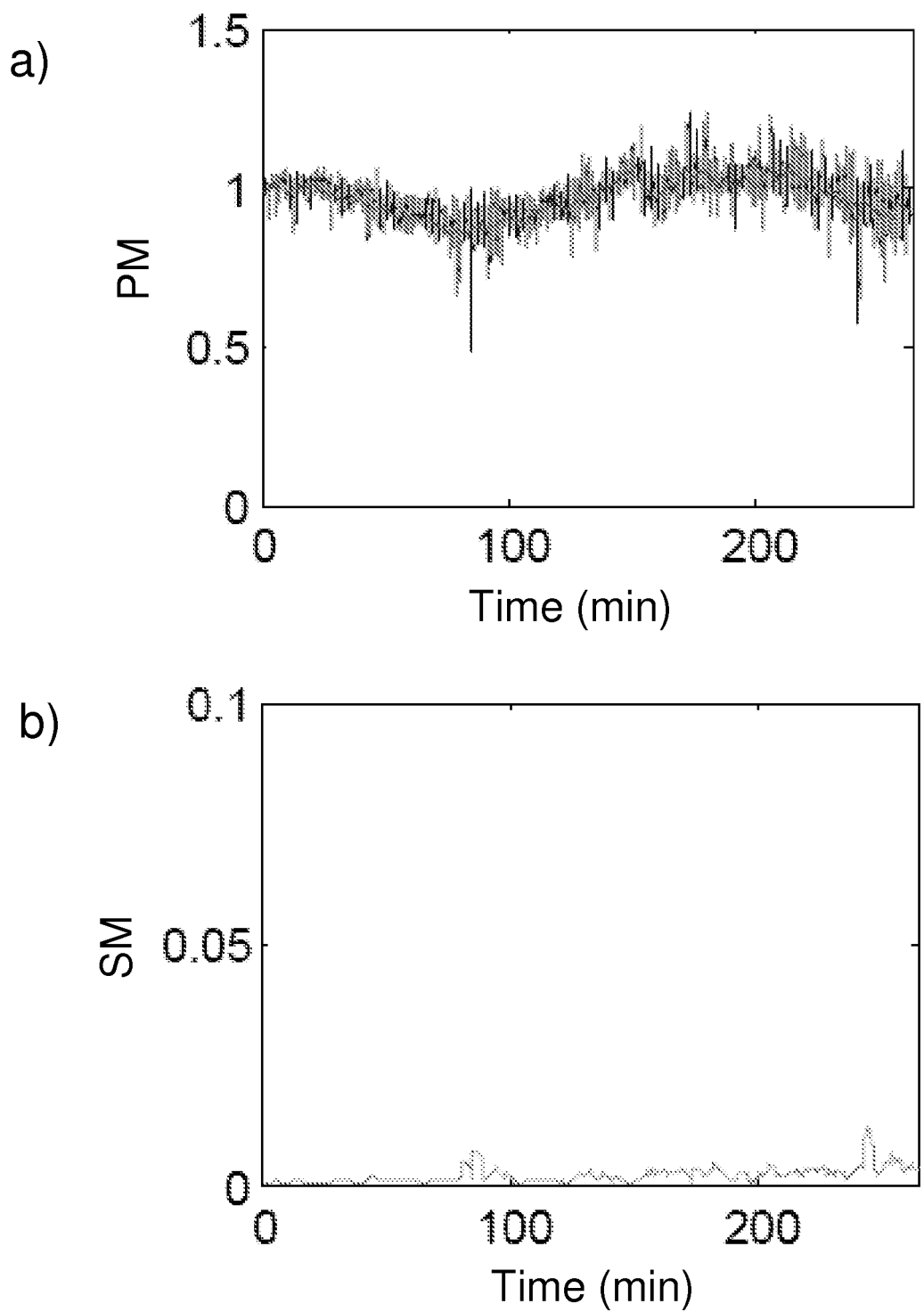
FIGS. 3a and 3b are plots of pulse magnitude and variance of pulse magnitude, respectively, obtained during a treatment with no hypotension event.
Figure 4:
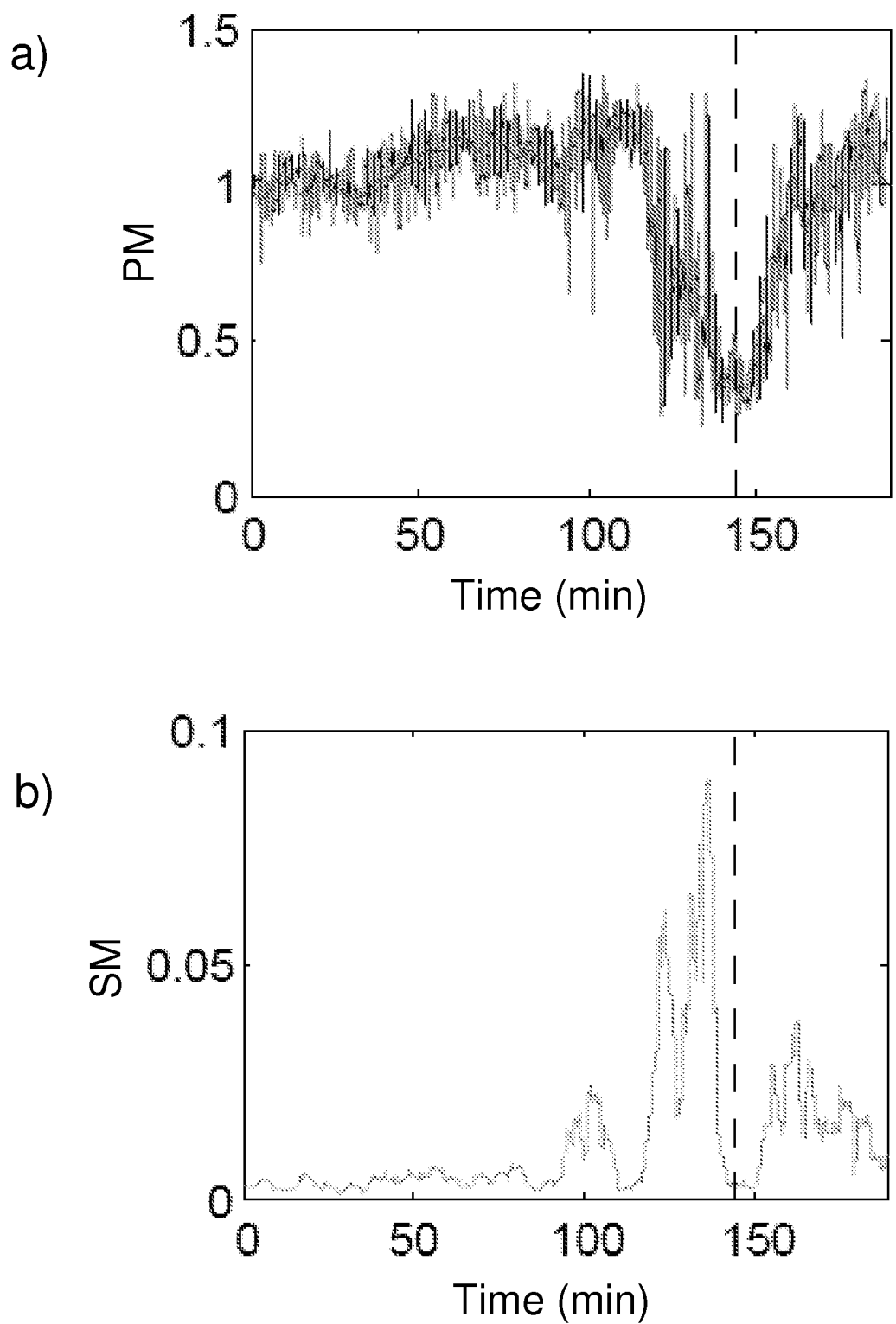
FIGS. 4a and 4b are plots of pulse magnitude and variance of pulse magnitude, respectively, obtained during a treatment with an hypotension event.

The method for prediction of intradialytic hypotension according to this embodiment is to monitor the variance, or some other statistical dispersion measure, of the short-term pulse magnitude variation and to investigate whether or not it fulfils a decision criterion. As seen in FIGS. 3-4, there is a significant increase in the variance prior to hypotension and a low variance in case of stable blood pressure, respectively.

The short-term variations in the pulse magnitude are mainly due to variations in cardiac output. Capillary vasoconstriction may also contribute to short-term variation in the pulse magnitude. It is hypothesised that the increase in variability of cardiac output and capillary vasoconstriction prior to a hypotension is caused by the increased variability in the pumping of blood from the heart and the autonomic regulation of vasoconstriction in response to the hemodynamic instability prior to a hypotension, respectively.

The short-term variations in the pulse magnitude may be more affected by cardiac output than by vasoconstriction, since the variations in cardiac output is on a beat-to-beat basis. The pulse magnitude measure PM may be more affected by vasoconstriction. Thus, these two measures may replace and/or supplement each other, and if combined the prediction performance may improve. The two measures may also be used to separate the two effects of cardiac output and vasoconstriction from each other or determining the sequence of the different events.

Of course, the short-term variations in the pulse magnitude may also be used as a sole marker for prediction of hypotension, thus neglecting the information from the pulse magnitude measure PM.

In addition, the short-term variations in the pulse magnitude may be used in combination with other measures as well such as bio impedance or relative blood volume (BVS).

III. Combination of Embodiments

The methods of the above-described embodiments may extract different information from cardiac output and capillary vasoconstriction. Thus, by combining the pulse magnitude (PM) embodiment and the statistical dispersion (SM) embodiment it may be possible to separate the two effects from each other. In addition, there are differences in the changes of cardiac output and capillary vasoconstriction from patient to patient. In one patient, the autonomic regulation in order to prevent a hypotension may be more focused on regulations in cardiac output and in another patient it may be more focused on regulations in capillary vasoconstriction. Thus, the ability to predict a hypotension may be better reflected in the pulse magnitude measure PM in one patient and in the variability of the pulse magnitude measures PM in another patient. By combining the pulse magnitude embodiment and the dispersion embodiment, the prediction performance would probably improve on a large general dialysis population. In addition, the robustness to artefacts may also be improved if the two main embodiments are combined.

It may be noted that the length of the time window (i.e. the length of the pulse shape parameters $p_{PS}$), as well as the overlap (or non-overlap) of time windows, may differ between the pulse magnitude embodiment and the dispersion embodiment. Thus, when combining these embodiments, one set of pulse magnitude measures may be calculated in the pulse magnitude embodiment, and another set of pulse magnitude measures may be calculated in the dispersion embodiment. In both embodiments, the time window may be selected to include at least part of at least one pulse. However, it is presently believed that the maximum number of pulses in the time window may be any one of about 20, 15, 10, 5 and 2 in the dispersion embodiment, in order for the dispersion measure to reflect the variability in pulse magnitude.

The present invention relates to embodiments for prediction of hypotension during extra-corporeal circulation by only utilizing signals of the pulse oximetry instrument.

By monitoring the relative magnitude or magnitude variation of the pulse signal S from start of a dialysis session and comparing the relative reduction of the magnitude to a threshold a hypotension alert/warning may be issued as the value goes below the threshold. Alternatively, an alert/warning is triggered as the magnitude variation of the pulse signal exceeds another threshold.

One effect with the present invention, when combining the pulse magnitude embodiment with the dispersion embodiment is that it thus enables separation of the phenomena behind hypotension.

All of the process steps, as well as any sub-sequence of steps, described with reference to the FIG. 8 above may be controlled by means of a programmed computer apparatus. Moreover, although the embodiments of the invention described above with reference to the drawings comprise computer apparatus and processes performed in computer apparatus, the invention thus also extends to computer programs, particularly computer programs on or in a carrier, adapted for putting the invention into practice. The program may be in the form of source code; object code, a code intermediate source and object code such as in partially compiled form, or in any other form suitable for use in the implementation of the process according to the invention. The carrier may be any entity or device capable of carrying the program. For example, the carrier may comprise a storage medium, such as a Flash memory, a ROM (Read Only Memory), for example a CD (Compact Disc) or a semiconductor ROM, an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

It is also conceivable that some or all process steps are fully or partially implemented by dedicated hardware, such as an FPGA, an ASIC, or an assembly of discrete electronic components (resistors, capacitors, operational amplifier, transistors, filters, etc), as is well-known in the art.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. A monitoring arrangement for predicting a symptomatic blood pressure decrease in a subject, the monitoring arrangement comprising:
 a pulse recording apparatus configured to repeatedly register a pulse shape parameter in a peripheral body part of the subject based on a pulse signal, wherein each registered pulse shape parameter is a sequence of signal values in a respective time window representing a segment in the pulse signal, wherein the pulse recording apparatus comprises a pulse oximetry instrument configured to register the pulse shape parameter based on light response variations in at least one blood vessel of the subject, and
 a control unit configured to receive a plurality of pulse shape parameters registered by the pulse recording apparatus, wherein each received pulse shape parameter represents a different sequence of signal values, the control unit comprising a processing unit configured to:
calculate, during a measurement period, a plurality of pulse magnitude measures based on the plurality of pulse shape parameters, each calculated pulse magnitude measure based on a different received pulse shape parameter registered by the pulse recording apparatus,
determine whether at least one of the plurality of calculated pulse magnitude measures fulfils a pulse magnitude decision criterion relative to a predetermined pulse magnitude reference measure,
calculate a statistical dispersion measure from the plurality of calculated pulse magnitude measures, wherein the statistical dispersion measure represents variability of a sequence of pulse magnitude measures in the plurality of calculated pulse magnitude measures,
determine whether the calculated statistical dispersion measure based on the plurality of pulse magnitude measures fulfils a statistical measure decision criterion relative to a reference predetermined statistical dispersion measure, and
generate a relative magnitude output signal indicating a prediction of a symptomatic blood pressure decrease in the subject in response to the plurality of pulse magnitude measures fulfilling a pulse magnitude decision criterion relative to a pulse magnitude reference measure,
and generate magnitude variation output signal indicating a prediction of a symptomatic blood pressure decrease in the subject in response to the calculated statistical dispersion measure based on the plurality of pulse magnitude measures fulfilling the statistical measure decision criterion relative to the reference predetermined statistical dispersion measure, wherein the relative magnitude output signal and the magnitude variation output signal each comprise an alarm triggering signal prompting performance of at least automatic actions, wherein fulfilment of the statistical measure decision criterion indicates a different physiological condition of the subject than fulfilment of the pulse magnitude decision criterion,
and
wherein the monitoring arrangement is connected to a dialysis machine comprising one or more systems in the dialysis machine configured to be activated by the alarm triggering signal to automatically perform at least one of a plurality of actions to counter-act an occurrence of a hypotension event in response to generation of an output signal indicating a prediction of a symptomatic blood pressure decrease in the subject, wherein the plurality of actions to counter-act an occurrence of a hypotension event comprises adjusting a rate of fluid removal from the subject by reducing and/or stopping a rate of fluid removal, increasing a conductivity in a dialysis fluid, supplying a saline bolus to a blood line connected to the cardiovascular system of the subject, adjusting a position of a controllable structure supporting the subject, and setting a dialysis monitor in bypass.

2. The arrangement according to claim 1, wherein the control unit is configured to calculate the statistical dispersion measure from the plurality of calculated pulse magnitude measures based on a variance, standard deviation, coefficient of variation, variance-to-mean, a sum of differences, an energy measure, or any combinations thereof of the plurality of calculated pulse magnitude measures.

3. The arrangement according to claim 1, wherein the control unit is configured to calculate each of the plurality of pulse magnitude measures based on at least one of a peak-to-peak measure, an integration measure, an energy measure, and a frequency spectrum intensity measure of a different received pulse shape parameter registered by the pulse recording apparatus.

4. The arrangement according to claim 1, wherein the processing unit further is configured to:
calculate an initial statistical dispersion measure as a function of a set of initial pulse magnitude measures based on the pulse shape parameters received at a first instance,
store the initial statistical dispersion measure in a memory apparatus associated with the control unit,
calculate, during the measurement period subsequent to the first instance, a respective statistical dispersion measure as a function of a respective set of the pulse magnitude measures, and
investigate, for each statistical dispersion measure in the measurement period, whether or not the measure fulfils the decision criterion, which is given relative to the initial statistical dispersion measure.

5. The arrangement according to claim 4, wherein the processing unit is configured to regard the decision criterion as fulfilled if:
an examined statistical dispersion measure of a given set of pulse magnitude measures and/or a sequence of examined statistical dispersion measures is above a threshold value calculated based on the initial statistical dispersion measure, and
a predetermined amount of the statistical dispersion measures of the pulse shape parameters received within a test period after the given set of pulse magnitude measures and/or the sequence of examined statistical dispersion measures is above the threshold value.

6. The arrangement according to claim 5, wherein the predetermined amount is a value representing approximately 50% to approximately 100% of the statistical dispersion measures of the pulse shape parameters received within the test period.

7. The arrangement according to claim 5, wherein the predetermined amount represents all the statistical dispersion measures of the pulse shape parameters received within the test period.

8. The arrangement according to claim 5, wherein the test period is an interval selected from a range extending from approximately one minute to approximately fifteen minutes.

9. The arrangement according to claim 5, wherein the processing unit is configured to calculate the threshold value by:
normalizing the initial statistical dispersion measure, and dividing the normalized statistical dispersion measure by a predefined denominator.

10. The arrangement according to claim 9, wherein the processing unit is configured to, during the measurement period, calculate a statistical dispersion measure by dividing an original measure with the initial statistical dispersion measure.

11. The arrangement according to claim 10, wherein the predefined denominator is a value selected from a range extending from approximately 0.2 to approximately 0.8.

12. The arrangement according to claim 5, wherein the threshold value is given by a predefined dispersion value.

13. The arrangement according to claim 1, wherein the control unit is further configured to:

investigate whether at least one of the calculated pulse magnitude measures fulfils a pulse magnitude decision criterion relative to a predetermined pulse magnitude reference measure, and generate the output signal as a function of both said statistical measure decision criterion and said pulse magnitude decision criterion.

14. The arrangement according to claim 1, wherein the arrangement comprises:

an auxiliary recording apparatus configured to repeatedly register a bio-impedance parameter representing a degree of contraction of the subject's capillary blood vessels, and the processing unit being further configured to receive the bio-impedance parameter, investigate whether or not the bio-impedance parameter fulfils an auxiliary alarm criterion, and if so, generate the output signal.

15. The arrangement according to claim 1, wherein the arrangement is adapted to predict symptomatic blood pressure decrease in a subject undergoing blood treatment, and the processing unit being configured to calculate the initial statistical dispersion measure based on a set of pulse magnitude measures calculated during an initial phase of the blood treatment.

16. A monitoring arrangement for predicting a symptomatic blood pressure decrease in a subject, the monitoring arrangement comprising:

a pulse recording apparatus configured to repeatedly register a pulse shape parameter in a peripheral body part of the subject based on a pulse signal, wherein each registered pulse shape parameter is a sequence of signal values in a respective time window representing a segment in the pulse signal, wherein the pulse recording apparatus comprises a pulse oximetry instrument configured to register the pulse shape parameter based on light response variations in at least one blood vessel of the subject, and a control unit configured to receive a plurality of pulse shape parameters registered by the pulse recording apparatus, wherein each received pulse shape parameter represents a different sequence of signal values, the control unit comprising a processing unit configured to:

calculate, during a measurement period, a plurality of pulse magnitude measures based on the plurality of pulse shape parameters, each calculated pulse magnitude measure based on a different received pulse shape parameter registered by the pulse recording apparatus, determine whether at least one of the plurality of calculated pulse magnitude measures fulfils a pulse magnitude decision criterion relative to a predetermined pulse magnitude reference measure, calculate a statistical dispersion measure from the plurality of calculated pulse magnitude measures, wherein the statistical dispersion measure represents variability of a sequence of pulse magnitude measures in the plurality of calculated pulse magnitude measures, determine whether the calculated statistical dispersion measure based on the plurality of pulse magnitude measures fulfils a statistical measure decision criterion relative to a reference predetermined statistical dispersion measure, and generate a relative magnitude output signal indicating a prediction of a symptomatic blood pressure decrease in the subject in response to the plurality of pulse magnitude measures fulfilling a pulse magnitude decision criterion relative to a pulse magnitude reference measure, and generate magnitude variation output signal indicating a prediction of a symptomatic blood pressure decrease in the subject in response to the calculated statistical dispersion measure based on the plurality of pulse magnitude measures fulfilling the statistical measure decision criterion relative to the reference predetermined statistical dispersion measure, wherein the relative magnitude output signal and the magnitude variation output signal each comprise an alarm triggering signal prompting performance of at least manual actions, wherein fulfilment of the statistical measure decision criterion indicates a different physiological condition of the subject than fulfilment of the pulse magnitude decision criterion, and wherein the monitoring arrangement is connected to an alarm unit comprising an alarm configured to be activated by the alarm triggering signal to prompt manual performance of at least one of a plurality of actions to counter-act an occurrence of a hypotension event in response to generation of an output signal indicating a prediction of a symptomatic blood pressure decrease in the subject, wherein the plurality of actions to counter-act an occurrence of a hypotension event comprises adjusting a rate of fluid removal from the subject by reducing and/or stopping a rate of fluid removal, increasing a conductivity in a dialysis fluid, supplying a saline bolus to a blood line connected to the cardiovascular system of the subject, adjusting a position of a controllable structure supporting the subject, and setting a dialysis monitor in bypass.

17. The arrangement according to claim 16, wherein the control unit is configured to calculate the statistical dispersion measure from the plurality of calculated pulse magnitude measures based on a variance, standard deviation, coefficient of variation, variance-to-mean, a sum of differences, an energy measure, or any combinations thereof of the plurality of calculated pulse magnitude measures.

18. The arrangement according to claim 16, wherein the control unit is configured to calculate each of the plurality of pulse magnitude measures based on at least one of a peak-to-peak measure, an integration measure, an energy measure, and a frequency spectrum intensity measure of a different received pulse shape parameter registered by the pulse recording apparatus.

19. The arrangement according to claim 16, wherein the processing unit further is configured to:

calculate an initial statistical dispersion measure as a function of a set of initial pulse magnitude measures based on the pulse shape parameters received at a first instance, store the initial statistical dispersion measure in a memory apparatus associated with the control unit, calculate, during the measurement period subsequent to the first instance, a respective statistical dispersion measure as a function of a respective set of the pulse magnitude measures, and investigate, for each statistical dispersion measure in the measurement period, whether or not the measure fulfils the decision criterion, which is given relative to the initial statistical dispersion measure.

20. The arrangement according to claim 19, wherein the processing unit is configured to regard the decision criterion as fulfilled if:

an examined statistical dispersion measure of a given set of pulse magnitude measures and/or a sequence of examined statistical dispersion measures is above a threshold value calculated based on the initial statistical dispersion measure, and a predetermined amount of the statistical dispersion measures of the pulse shape parameters received within a test period after the given set of pulse magnitude measures and/or the sequence of examined statistical dispersion measures is above the threshold value.

21. The arrangement according to claim 20, wherein the predetermined amount is a value representing approximately 50% to approximately 100% of the statistical dispersion measures of the pulse shape parameters received within the test period.

22. The arrangement according to claim 20, wherein the predetermined amount represents all the statistical dispersion measures of the pulse shape parameters received within the test period.

23. The arrangement according to claim 20, wherein the test period is an interval selected from a range extending from approximately one minute to approximately fifteen minutes.

24. The arrangement according to claim 20, wherein the processing unit is configured to calculate the threshold value by:

normalizing the initial statistical dispersion measure, and
dividing the normalized statistical dispersion measure by a predefined denominator.

25. The arrangement according to claim 24, wherein the processing unit is configured to, during the measurement period, calculate a statistical dispersion measure by dividing an original measure with the initial statistical dispersion measure.

26. The arrangement according to claim 25, wherein the predefined denominator is a value selected from a range extending from approximately 0.2 to approximately 0.8.

27. The arrangement according to claim 20, wherein the threshold value is given by a predefined dispersion value.

28. The arrangement according to claim 16, wherein the control unit is further configured to:

investigate whether at least one of the calculated pulse magnitude measures fulfils a pulse magnitude decision criterion relative to a predetermined pulse magnitude reference measure, and generate the output signal as a function of both said statistical measure decision criterion and said pulse magnitude decision criterion.

29. The arrangement according to claim 16, wherein the arrangement comprises:

an auxiliary recording apparatus configured to repeatedly register a bio-impedance parameter representing a degree of contraction of the subject's capillary blood vessels, and the processing unit being further configured to receive the bio-impedance parameter, investigate whether or not the bio-impedance parameter fulfils an auxiliary alarm criterion, and if so, generate the output signal.

30. The arrangement according to claim 16, wherein the arrangement is adapted to predict symptomatic blood pressure decrease in a subject undergoing blood treatment, and the processing unit being configured to calculate the initial statistical dispersion measure based on a set of pulse magnitude measures calculated during an initial phase of the blood treatment.

* * * * *